(12) United States Patent
Khan et al.

(10) Patent No.: US 12,237,059 B2
(45) Date of Patent: Feb. 25, 2025

(54) SECURE USER-CONTROLLED PERSONAL HEALTH RECORDS

(71) Applicant: AT&T Intellectual Property I, L.P., Atlanta, GA (US)

(72) Inventors: Sameena Khan, Peachtree Corners, GA (US); Zhi Cui, Sugar Hill, GA (US); Bo Lee, Alpharetta, GA (US)

(73) Assignee: AT&T Intellectual Property I, L.P., Atlanta, GA (US)

( * ) Notice: Subject to any disclaimer, the term of this patent is extended or adjusted under 35 U.S.C. 154(b) by 267 days.

(21) Appl. No.: 17/548,634

(22) Filed: Dec. 13, 2021

(65) Prior Publication Data

US 2023/0187038 A1 Jun. 15, 2023

(51) Int. Cl.
*G16H 10/00* (2018.01)
*G16H 10/65* (2018.01)

(52) U.S. Cl.
CPC ................... *G16H 10/65* (2018.01)

(58) Field of Classification Search
CPC ......... G16H 10/00; G16H 10/65; G16H 10/60
See application file for complete search history.

(56) References Cited

U.S. PATENT DOCUMENTS

| | | | | |
|---|---|---|---|---|
| 7,805,377 | B2 * | 9/2010 | Felsher ................... | G06Q 10/10 705/64 |
| 8,090,590 | B2 * | 1/2012 | Fotsch ................... | G06Q 40/08 705/2 |
| 8,949,137 | B2 * | 2/2015 | Crapo ................... | G16H 40/20 705/3 |
| 9,268,906 | B2 * | 2/2016 | Curran ................... | G16H 50/70 |
| 11,894,129 | B1 * | 2/2024 | Dunstan ................ | G16H 50/20 |
| 2004/0267572 | A1 * | 12/2004 | Emery ................... | G06Q 10/1095 705/2 |

(Continued)

FOREIGN PATENT DOCUMENTS

| | | | | |
|---|---|---|---|---|
| AU | 2015101556 A4 | * | 11/2015 | ............... H04B 1/38 |
| CA | 2816315 A1 | * | 3/2007 | ............. G16H 10/60 |

(Continued)

OTHER PUBLICATIONS

S. Usharani; S. Prithivi; S. Sharmila; P. Manju Bala; T. Ananth Kumar; R. Rhajmohan, Mobile Application for Doctor Appointment Scheduling (Ensglis), 2021 International Conference on System, Computation, Automation and Networking (ICSCAN) (2021, pp. 1-6), Jul. 30, 2021 (Year: 2021).*

Mohammed Alkhawlani; Wesam Ali Husien; Saba Noori Alhamdany, Facilitating Patient Registrations Using an Integrating Healthcare Management System (English), 2018 1st Annual International Conference on Information and Sciences (AiCIS) (2018, pp. 23-27), Nov. 1, 2018 (Year: 2018).*

(Continued)

*Primary Examiner* — Marilyn G Macasiano
(74) *Attorney, Agent, or Firm* — Hartman & Citrin LLC

(57) ABSTRACT

The concepts and technologies disclosed herein are directed to secure user-controlled personal health records ("PHRs"). According to one aspect disclosed herein, a patient device can launch a PHR wallet device application. The patient device can connect, via the PHR wallet device application, to a PHR server that stores PHRs associated with a user. The patient device can define, via the PHR wallet device application, an access level to be applied to the PHR. The patient device can initiate, via the PHR wallet device application, a transfer of the PHR from the PHR server to a health care provider. The health care provider can be permitted to access the portion of the PHR in accordance with the access level.

20 Claims, 6 Drawing Sheets

(56) References Cited

U.S. PATENT DOCUMENTS

| | | | | |
|---|---|---|---|---|
| 2005/0027567 A1* | 2/2005 | Taha | ............ | G16H 10/20 |
| | | | | 705/2 |
| 2009/0024417 A1* | 1/2009 | Marks | ............ | G16H 10/60 |
| | | | | 705/2 |
| 2013/0103427 A1* | 4/2013 | Lorsch | ............ | G16H 20/10 |
| | | | | 705/3 |
| 2013/0124228 A1* | 5/2013 | Lorsch | ............ | G06Q 10/10 |
| | | | | 705/3 |
| 2018/0052958 A1* | 2/2018 | Crawford | ............ | G16H 40/63 |
| 2018/0211718 A1* | 7/2018 | Heath | ............ | G16H 80/00 |
| 2020/0258605 A1* | 8/2020 | Blechman | ............ | G16H 40/67 |

FOREIGN PATENT DOCUMENTS

| | | | | | |
|---|---|---|---|---|---|
| KR | 2008-0068653 A | * | 7/2009 | ............ | G06Q 50/00 |
| MX | 2008003495 A | * | 10/2008 | ............ | G06F 19/00 |
| WO | WO 2007/024555 A2 | * | 3/2007 | ............ | G16H 10/60 |

OTHER PUBLICATIONS

Tulu, B.; Strong, D.; Johnson, S.; Bar-On, I.; Trudel, J.; Garber, L., Personal Health Records: Identifying Utilization Patterns from Sysytem Use Logs and Patient Interviews )English), 2012 45th Hawaii International Conference on System Sciences (2012, pp. 2716-2725), Jan. 1, 2012 (Year: 2012).*

Cernian, Alexandra; Tiganoaia, Bogdan; Sacala, Ioan; Pavel, Adrian; Iftemi, Alin, PatiendDataChain: A Blochchain-Based Approach to Integrate Personal Health Records (English), Sensors (Basel, Switzerland), 20(22), 6538, Nov. 16, 2020 (Year: 2020).*

S. Osebe; C. M. Wachira; F. Matu; N. Bore; D. Kaguma; J. Mutahi, W. Ogallo; C. Cintas; S. L. Remy; A. Walcott; K. Weldemariam, Enabling Care Continuity using a Digital Health Wallet (English), 2019 IEEE International Conference on Healthcare Informatics (ICHI) (2019, pp. 1-7), Jun. 1, 2019 (Year: 2019).*

* cited by examiner

SECURE USER-CONTROLLED PERSONAL HEALTH RECORDS

BACKGROUND

Health data is considered one of the most sensitive types of data about an individual, and under the Health Insurance Portability and Accountability Act ("HIPAA") in the United States, this data must be protected with confidentiality. Currently, an individual may share personal identifying data (e.g., name, physical address, telephone number, email address, social security number, and the like) and health data (e.g., pre-existing condition(s), medications, personal medical history, family medical history, genetic predispositions, and the like) with multiple health care providers, such as doctors, nurses, radiography technicians, pharmacists, and the like. In this manner, an individual may have little to no control over what data is shared and how the data is stored. Moreover, an individual cannot easily delete their data once they decide to stop using a particular health care provider or facility, including, for example, scenarios in which the individual moves to a different location, must change providers for insurance reasons, or desires to change for other reasons such as a bad experience.

While hospitals and other medical facilities may use walled gardens to control access to patient health data, a more recent approach is to allow health care providers access to patient health data that has been anonymized. After patient health data are anonymized and can no longer be linked to a specific patient, the patient health data may be rendered useless to a malicious attacker. However, access to patient health data is crucial in emergency situations, and the anonymity of patient health data may prove troublesome if the patient is unable to provide identification when they require immediate treatment. Certain health data may be vital for first responders or for doctors to provide an immediate, accurate diagnosis and proper treatment. While the need for accurate health data for care is clear, threats from identity theft and lawsuits have made it critical to protect the personal data of patients throughout the diagnostic and treatment processes.

SUMMARY

Concepts and technologies disclosed herein are directed to secure user-controlled personal health records ("PHRs"). According to one aspect disclosed herein, a patient device can launch a PHR wallet device application. The patient device can connect, via the PHR wallet device application, to a PHR server that stores a PHR associated with a patient. The patient device can define, via the PHR wallet device application, an access level to be applied to the PHR. The patient device can initiate, via the PHR wallet device application, a transfer of the PHR from the PHR server to a health care provider. The health care provider can be permitted to access the portion of the PHR in accordance with the access level.

In some embodiments, the PHR includes personal identifying data and health data. The access level can permit access to at least a portion of the health data, at least a portion of the personal identifying data, or at least a portion of the health data and at least a portion of the personal identifying data.

In some embodiments, the patient device can define, via the PHR wallet device application, a policy that specifies a plurality of access levels and a condition under which each access level of the plurality of access levels is to be applied. The plurality of access levels can include the access level. The condition can define a type of health care provider, a time period, and/or a trigger event. In some embodiments, the policy can be assigned to a profile. The profile can include multiple policies.

In some embodiments, the patient device can receive a notification identifying new health data to be added to the PHR. The new health data can be provided, for example, by the health care provider or a new health care provider.

In some embodiments, the patient device can disable, via the PHR wallet device application, access to the PHR by the health care provider. The patient device can reenable access to the PHR as needed.

It should be appreciated that the above-described subject matter may be implemented as a computer-controlled apparatus, a computer process, a computing system, or as an article of manufacture such as a computer-readable storage medium. These and various other features will be apparent from a reading of the following Detailed Description and a review of the associated drawings.

This Summary is provided to introduce a selection of concepts in a simplified form that are further described below in the Detailed Description. This Summary is not intended to identify key features or essential features of the claimed subject matter, nor is it intended that this Summary be used to limit the scope of the claimed subject matter. Furthermore, the claimed subject matter is not limited to implementations that solve any or all disadvantages noted in any part of this disclosure.

DETAILED DESCRIPTION

Figure 1:
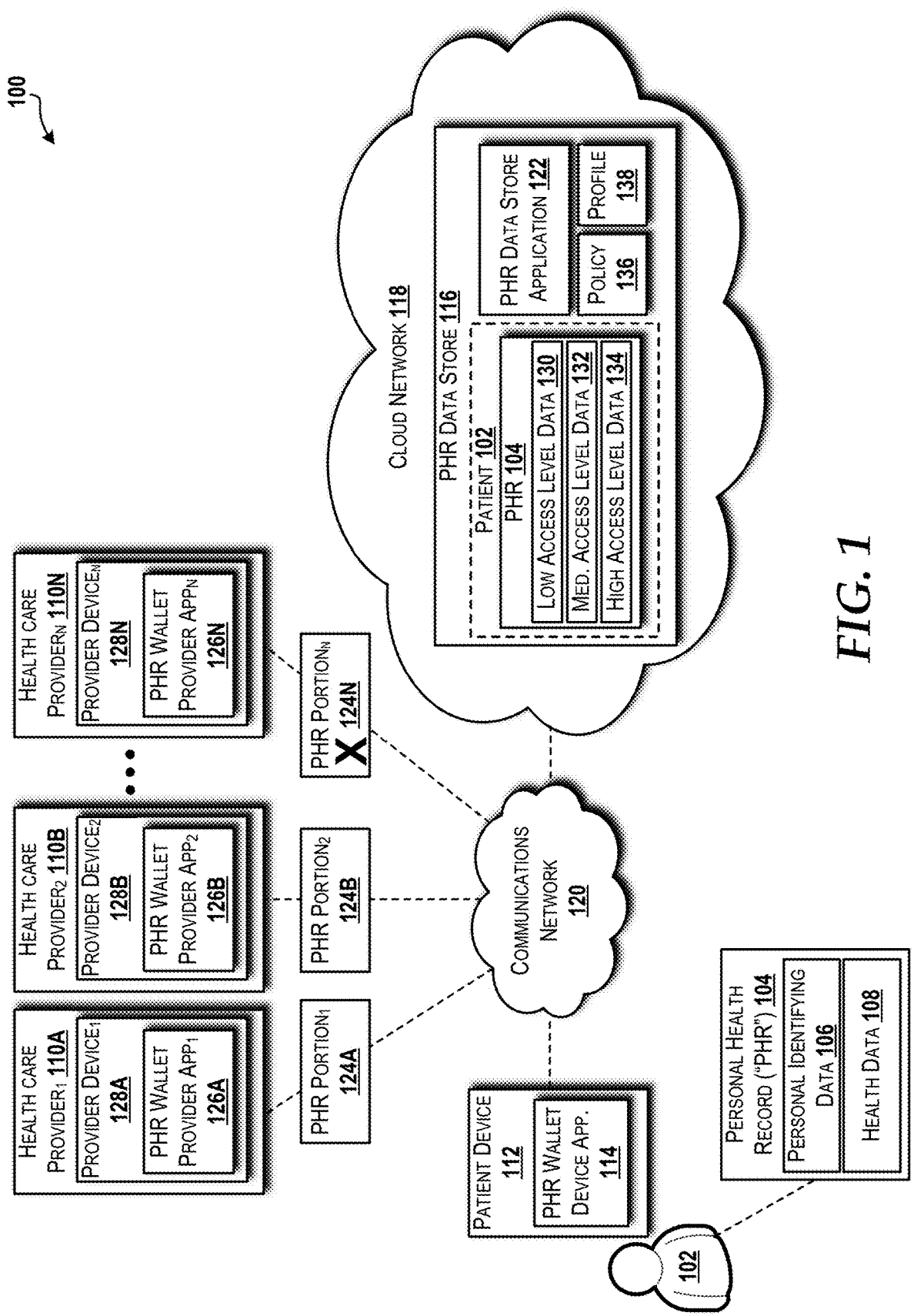
FIG. 1 is a block diagram illustrating an illustrative operating environment in which the concepts and technologies disclosed herein can be implemented.

Personal identifying data and health data is commonly shared with health care providers. If a patient decides to use a different provider (e.g., due to a change in insurance coverage, a relocation, or patient preference), the patient can request that their data be deleted or otherwise destroyed, but the patient has no direct control over how their data is handled. For these and other reasons, patients desire to have complete ownership of their data so that the patient can allow doctors, nurses, pharmacists, hospitals, interfacing medical facilities, and other medical-related entities to have complete access to meaningful, relevant information in a secure, easy-to-use, and centralized transaction location. Moreover, patients desire the controls necessary to grant and deny access to their data at their sole discretion.

The concepts and technologies disclosed herein are directed to secure user-controlled personal health records ("PHRs"). In some embodiments, a wallet application facilitates the transformation from having PHRs in disparate medical facilities to secure ownership of this data in a centralized location, such as a personal cloud network. The concepts and technologies disclosed herein replace the need for physical and digital health records that are commonly used in doctor's offices, hospitals, interfacing facilities, pharmacies, and the like with complete control and access management of PHRs owned exclusively by the patients themselves. Aspects of the concepts and technologies disclosed herein can benefit from future generation cellular technologies, such as 6G and beyond, which can enable trustworthy, secure network and communications with cloud resources.

While the subject matter described herein may be presented, at times, in the general context of program modules that execute in conjunction with the execution of an operating system and application programs on a computer system, those skilled in the art will recognize that other implementations may be performed in combination with other types of program modules. Generally, program modules include routines, programs, components, data structures, computer-executable instructions, and/or other types of structures that perform particular tasks or implement particular abstract data types. Moreover, those skilled in the art will appreciate that the subject matter described herein may be practiced with other computer systems, including handheld devices, mobile devices, wireless devices, multiprocessor systems, distributed computing systems, microprocessor-based or programmable consumer electronics, minicomputers, mainframe computers, routers, switches, other computing devices described herein, and the like.

In the following detailed description, references are made to the accompanying drawings that form a part hereof, and in which are shown by way of illustration specific embodiments or examples. Referring now to the drawings, in which like numerals represent like elements throughout the several figures, aspects of concepts and technologies for secure user-controlled PHRs will be described.

Turning now to FIG. 1, an operating environment 100 in which aspects of the concepts and technologies disclosed herein can be implemented will be described, according to an illustrative embodiment. The operating environment 100 includes a patient 102 who is also referred to herein as a user 102. The patient 102 is associated with a PHR 104 that can include personal identifying data 106 and health data 108. The personal identifying data 106 can include any data that can be used, at least in part, to obtain an identifying characteristic of the patient 102. Some non-limiting examples of personal identifying data 106 include name, physical address, telephone number, email address, social security number, biometric data, and the like. The health data 108 can include any data associated with one or more aspects of the health of the patient 102. The health data 108 can include historical health data and/or current health data. The health data 108 can identify basic body attributes (e.g., height, weight, body mass index, etc.) pre-existing condition(s), current conditions (e.g., sick with flu-like symptoms), current medications, medication history, vaccination history, specialist history (e.g., oncologist), personal medical history, family medical history, surgical history, genetic predispositions, and the like. The health data 108 can include specific details about the health of the patient 102, including laboratory results, vital sign measurements (e.g., heart rate, blood oxygen level, body temperature, blood pressure, and the like). The health data 108 can include data obtained by one or more remote patient monitoring devices (not shown). For example, the patient 102 may have a glucose monitor that measures glucose levels every X minutes.

Typically, the patient 102 would provide, often in handwritten form, the personal identifying data 106 and the health data 108 in preparation for seeing a health care provider 110. This data may be stored in a physical file folder associated with the patient 102 or manually entered into a patient database. Some health care providers 110 may provide a web portal or device application through which the patient 102 can provide this data. Often times the patient 102 then has to duplicate the personal identifying data 106 and the health data 108 for each health care provider 110 they visit. In some instances, the health care provider 110 may be part of an organization that includes a number of hospitals, urgent care facilities, pharmacies, primary care physicians, specialty physicians, and/or the like. In these instances, the patient 102 may only need to provide the personal identifying data 106 and the health data 108 to one health care provider 110, and this data can be disseminated, as needed, to other health care providers within the organization. Moreover, due to certain insurance requirements, the patient 102 may be required to update the personal identifying data 106 and/or health data 108 on a yearly basis. In the illustrated example, three health care providers 110A-110N are shown. It should be understood, however, that the concepts and technologies disclosed herein provide a suitable solution for any number of health care providers 110 to access any number of PHRs 104 associated with any number of patients 102, such as the PHR 104 associated with the patient 102 in the illustrated example.

Figure 4:
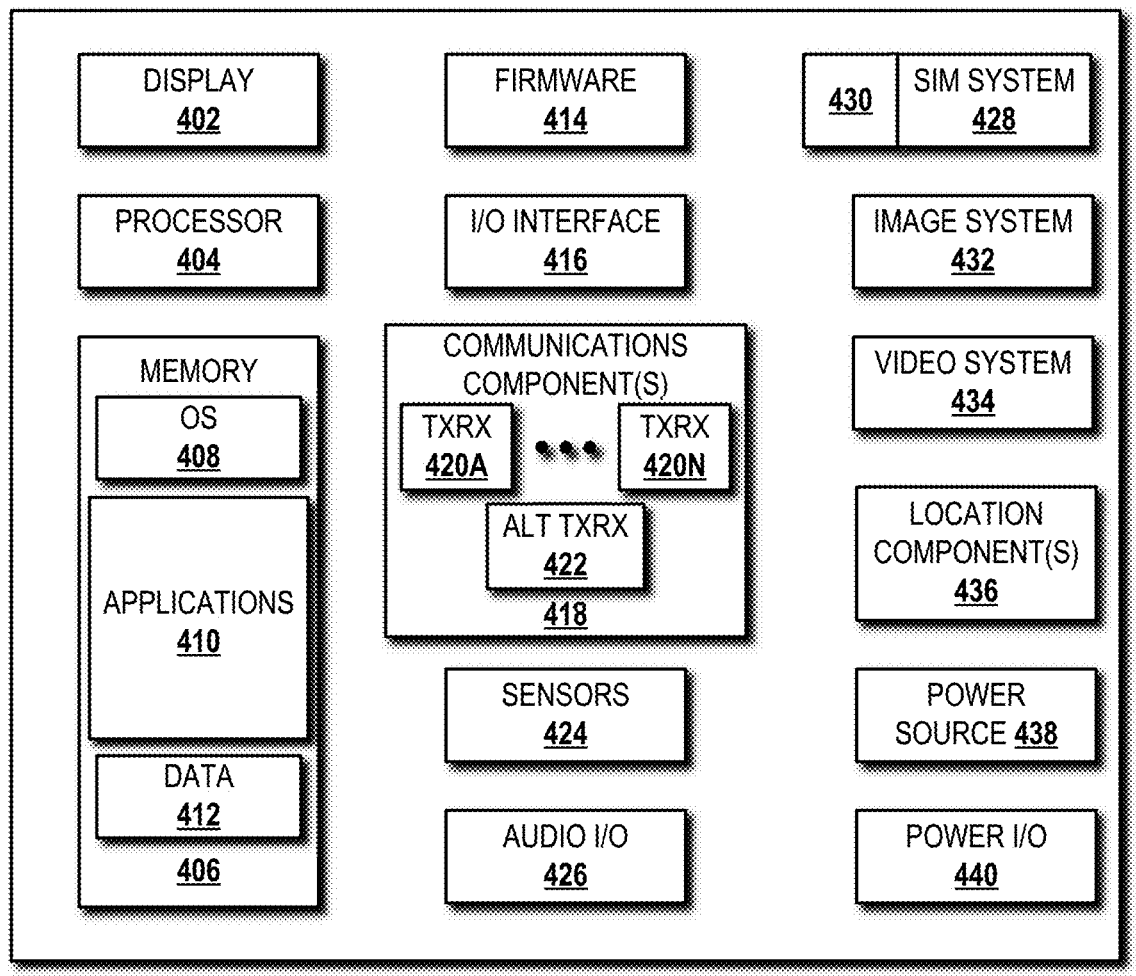
FIG. 4 is a block diagram illustrating an example mobile device and components thereof capable of implementing aspects of the embodiments presented herein.

The patient 102 can be associated with a patient device 112, which may be embodied as a mobile device such as a smartphone (best shown in FIG. 4) or other computing device such as a tablet or personal computer (best shown in FIG. 4). The patient device 112 can execute a PHR wallet device application 114 that enables the patient 102 to control access to the PHR 104 that is stored in a centralized location, such as a PHR data store 116, which may operate as a standalone data store or as part of a cloud network 118 as shown in the illustrated example. Although only a single patient device 112 is illustrated, the patient 102 may have access to multiple patient devices 112, each of which can be configured with a PHR wallet device application 114. In this manner, the patient 102 is not tied to a specific device and may utilize multiple devices to control access to the PHR 104.

The PHR wallet device application 114 can be embodied as a native application that may be downloaded or otherwise transferred to the patient device 112 from an application marketplace, a website, a network, another device (e.g., a solid state storage device), a physical medium, or the like. The PHR wallet device application 114 can be embodied as a web application and can be made accessible via a web address (i.e., a uniform resource locator). In either case, the PHR wallet device application 114 provides a client-side interface through which the patient 102 can control access to the PHR 104 stored on the PHR data store 116.

In some embodiments, the cloud network 118 is a personal cloud network that is accessible only by the patient 102. In these embodiments, the cloud network 118 may be hosted by a cloud hosting platform or self-hosted by the patient 102 on appropriate hardware (not shown). In other embodiments, the cloud network 118 is a public cloud network, a private cloud network, or a hybrid cloud network. As used herein, a "private cloud network" is a cloud network that is provisioned for use by a select one or more users, such as the patient 102. As used herein, a "public cloud network" is a cloud network that is provisioned for public use—that is, anyone (e.g., the patient 102) who wants to use or purchase access. In any case, the PHR(s) 104 can be securely stored such that access is controlled solely by the patient 102 via the PHR wallet device application 114.

The patient device 112 can connect to the PHR data store 116 directly or through the cloud network 118 via a communications network 120. The communications network 120 is intended to broadly encompass one or more cellular networks, packet data networks such as the Internet, and other intervening networks. In some embodiments, the communications network 120 is embodied, at least in part, as a network 500 shown in FIG. 5. In some embodiments, the communications network 120 operates in accordance with one or more standards specifications, such as defined by Third Generation Partnership Program ("3GPP"), including current and future generation technologies such as, but not limited to, those technologies described and/or marketed under 3G, 4G, 5G, 6G, and xG monikers.

The PHR data store 116 can store the PHR 104 for a single patient, such as the patient 102 in the illustrated example, or multiple PHRs 104 for multiple patients 102. The PHR data store 116 can be implemented as a simple data repository, a database, or other suitable data structure. In the illustrated example, the PHR data store 116 is managed, at least in part, via a PHR data store application 122. The PHR wallet device application 114 can interface with the PHR data store application 122 to enable the patient 102 to access and manage the PHR 104.

The patient 102 can dynamically grant and deny permission for the health care providers 110 to access all or at least a portion of the PHR 104. In the illustrated example, based upon permissions defined by the patient 102, a first health care provider 110A (shown as "health care provider" 110A") can access a first PHR portion 124A (shown as "PHR portion" 124A") of the PHR 104 via a first PHR wallet provider application 126A (shown as "PHR wallet provider application" 126A") executing on a first provider device 128A (shown as "provider device" 128A"); a second health care provider 110B (shown as "health care providers 110B") can access a second PHR portion 124B (shown as "PHR portions 124B") of the PHR 104 via a second PHR wallet provider application 126B (shown as "PHR wallet provider applications 126B") executing on a second provider device 128B (shown as "provider devices 128B"); and an $n^{th}$ health care provider$_n$ 110N (shown as "health care provider$_N$ 110N") can no longer access (i.e., permission has been withdrawn/denied) an $n^{th}$ portion 124N (shown as "PHR portion$_N$ 124N") of the PHR 104 via an $n^{th}$ PHR wallet provider application 126N (shown as "PHR wallet provider application 126N") executing on an $n^{th}$ provider device 128N (shown as "provider device$_N$ 128N").

The provider devices 128A-128N can be or can include mobile devices (e.g., smartphones, tablets, and the like), personal computers, and/or medical equipment. The PHR wallet provider applications 126 may require the health care providers 110 to enter access credentials such as username, password, personal identification number, biometric identification, any combination thereof, and/or the like. Other credentials may require verification, such as medical professional credentials, including medical school, graduate medical education, specialty board certifications, state licensure data and sanctions, Drug Enforcement Administration ("DEA") registration, National Provider Identifier ("NPI") number, combinations thereof, and/or the like. For other medical professionals, such as Emergency Medical Technicians ("EMTs"), Paramedics, and other medical professionals that are "in-the-field" for Ambulance, Fire, and/or other Emergency Services, the medical professional credentials may include credentials such as a FIRSTNET subscriber identity module ("SIM") identifier that can be used to provide, quick, trustworthy verification in-the-field.

In some embodiments, the patient 102 can grant access permissions in-person. For example, the PHR wallet device application 114 can present, on a display (best shown as display 402 in FIG. 4), a QR code that can be scanned by the PHR wallet provider application 126 using a camera of the provider device 128. As another example, the PHR wallet device application 114 may communicate with the PHR wallet provider application 126 via BLUETOOTH, near-field communications, local WI-FI, a wired connection, or the like to grant and remove permissions.

The PHR 104 can be divided into multiple access levels. It should be understood, however, that any number of access levels having any categorization criteria are contemplated. In the illustrated example, the PHR 104 includes low access level data 130, medium access level data 132, and high access level data 134. The patient 102 can define what portion(s) of the PHR 104 should be labeled as part of the low access level data 130, the medium access level data 132, and the high access level data 134. For example, the personal identifying data 106 shared as part of the low access level data 130 may include an age (e.g., 50 years old) instead of a birthday (e.g., May 4, 1971) that is shared only as part of the medium access level data 132 or higher. As another example, the health data 108 shared as part of the low access level data 130 may include a summary of the health data 108, whereas the health data 108 shared as part of the high access level data 134 may include a detailed account of the health data 108. The access levels can be assigned globally (i.e., across all health care providers 110), independently for each health care provider 110, or based on a group of two or more health care providers 110. The access levels can be increased or decreased at the discretion of the patient 102.

Although the patient 102 may manually manage permissions, the patient 102 may desire to automate all or at least a portion of this process. In some embodiments, the patient 102 can define one or more policies 136 that specify who can access the low access level data 130, the medium access level data 132, and the high access level data 134. The policies 136 can further define one or more conditions under which data is to be assigned to each available access level. The conditions can be time-based (e.g., only for a specified time period) and/or location-based (e.g., only at a certain location as determined by the patient device 112 via a location determining technology such as GPS). Custom conditions can be defined by the patient 102.

The patient 102 also can define one or more profiles 138, each of which can be used to enable one or more of the policies 136. For example, the patient 102 may have one profile for a primary care physician, another profile for a pharmacist, another profile for emergency rooms, and another profile for a specialist (e.g., an oncologist). The patient 102 can enable/disable profiles via the PHR wallet device application 114.

Figure 2:
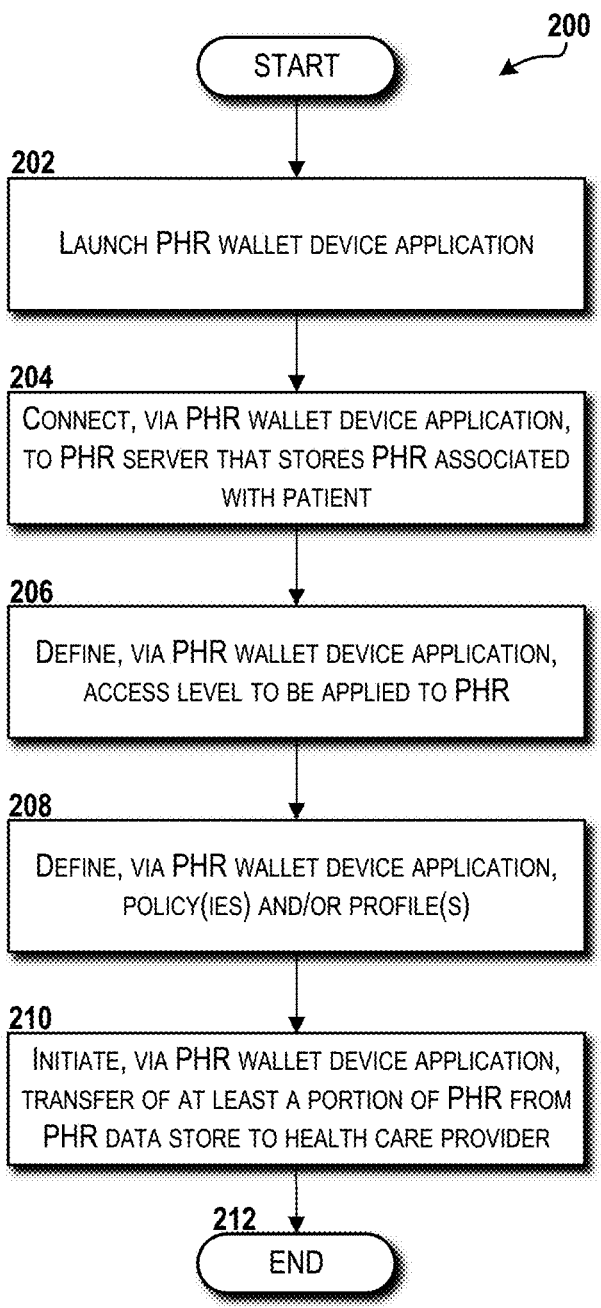
FIG. 2 is a flow diagram illustrating aspects of a method for providing secure user-controlled PHRs, according to an illustrative embodiment.

Turning now to FIG. 2, a method 200 for providing secure user-controlled PHRs will be described, according to an exemplary embodiment. It should be understood that the operations of the methods disclosed herein are not necessarily presented in any particular order and that performance of some or all of the operations in an alternative order(s) is possible and is contemplated. The operations have been presented in the demonstrated order for ease of description and illustration. Operations may be added, omitted, and/or performed simultaneously, without departing from the scope of the concepts and technologies disclosed herein.

It also should be understood that the methods disclosed herein can be ended at any time and need not be performed in its entirety. Some or all operations of the methods, and/or substantially equivalent operations, can be performed by execution of computer-readable instructions included on a computer storage media, as defined herein. The term "computer-readable instructions," and variants thereof, as used herein, is used expansively to include routines, applications, application modules, program modules, programs, components, data structures, algorithms, and the like. Computer-readable instructions can be implemented on various system configurations including single-processor or multiprocessor systems, minicomputers, mainframe computers, personal computers, hand-held computing devices, microprocessor-based, programmable consumer electronics, combinations thereof, and the like.

Thus, it should be appreciated that the logical operations described herein are implemented (1) as a sequence of computer implemented acts or program modules running on a computing system and/or (2) as interconnected machine logic circuits or circuit modules within the computing system. The implementation is a matter of choice dependent on the performance and other requirements of the computing system. Accordingly, the logical operations described herein are referred to variously as states, operations, structural devices, acts, or modules. These states, operations, structural devices, acts, and modules may be implemented in software, in firmware, in special purpose digital logic, and any combination thereof. As used herein, the phrase "cause a processor to perform operations" and variants thereof is used to refer to causing one or more processors disclosed herein to perform operations.

For purposes of illustrating and describing some of the concepts of the present disclosure, the methods disclosed herein may be described as being performed, at least in part, by one of the processors via execution of one or more software modules. It should be understood that additional and/or alternative devices and/or network nodes can provide the functionality described herein via execution of one or more modules, applications, and/or other software. Thus, the illustrated embodiments are illustrative, and should not be viewed as being limiting in any way.

The method 200 begins and proceeds to operation 202. At operation 202, the patient device 112 launches the PHR wallet device application 114. The patient device 112 can launch the PHR wallet device application 114 in response to input from the patient 102, such as the patient 102 selecting a display icon associated with the PHR wallet device application 114, the patient 102 issuing a voice command to launch the PHR wallet device application 114, or other direct input from the patient 102. The patient device 112 can launch the PHR wallet device application 114 in response to other triggers such as time-based triggers and/or location-based triggers. For example, the patient device 112 can launch the PHR wallet device application 114 at a time obtained from appointment information (e.g., scheduled doctor's appointment) contained in a calendar entry, task list, or the like. When the patient device 112 is authorized to launch the PHR wallet device application 114 can be specified as part of a setup process of the PHR wallet device application 114 and/or on an individual basis such as when a calendar entry is added to a calendar application on the patient device 112 or when a task is added to a task list application on the patient device 112. Location-based triggers can be based on location data obtained by the patient device 112 via GPS, triangulation, location beacons, and/or other location determining techniques.

From operation 202, the method 200 proceeds to operation 204. At operation 204, the patient device 112 connects, via the PHR wallet device application 114, to the PHR data store 116 that stores the PHR 104 associated with the patient 102. As mentioned above, the PHR data store 116 can be a standalone data store or can be part of a cloud network 118. In some embodiments, the PHR wallet device application 114 can prompt the patient 102 to provide authentication credentials such as, but not limited to, username, email address, password, personal identification number ("PIN"), two-factor authentication code (e.g., obtained via text message, email, or authenticator application), biometrics (e.g., facial recognition, voice recognition, and/or fingerprint recognition), any combination thereof, and/or the like.

From operation 204, the method 200 proceeds to operation 206. At operation 206, the patient device 112, via the PHR wallet device application 114, defines one or more access levels to be applied to the personal identifying data 106 and/or the health data 108 stored at the PHR data store 116 as part of the PHR 104 associated with the patient 102. It should be understood that the patient 102 may define, redefine, delete, and otherwise manage access levels as needed. In the example shown in FIG. 1, the PHR 104 includes low access level data 130, medium access level data 132, and high access level data 134. The patient 102 can define what portion(s) of the PHR 104 should be labeled as part of the low access level data 130, the medium access level data 132, and the high access level data 134. For example, the personal identifying data 106 shared as part of the low access level data 130 may include an age (e.g., 50 years old) instead of a birthday (e.g., May 4, 1971) that is shared only as part of the medium access level data 132 or higher. As another example, the health data 108 shared as part of the low access level data 130 may include a summary of the health data 108, whereas the health data 108 shared as part of the high access level data 134 may include a detailed account of the health data 108. The access levels can be assigned globally (i.e., across all health care providers 110), independently for each health care provider 110, or based on a group of two or more health care providers 110. The access levels can be increased or decreased at the discretion of the patient 102.

From operation 206, the method 200 proceeds to operation 208. At operation 208, the patient device 112 defines, via the PHR wallet device application 114, one or more policies 136 and/or one or more profiles 138 based upon input provided by the patient 102. Although the patient 102 may manually manage permissions, the patient 102 may desire to automate all or at least a portion of this process. As such, the patient 102 can define one or more policies 136 that specify who can access the low access level data 130, the medium access level data 132, and the high access level data 134. The policies 136 can further define one or more conditions under which data is to be assigned to each available access level. The conditions can be time-based (e.g., only for a specified time period) and/or location-based (e.g., only at a certain location as determined by the patient device 112 via a location determining technology such as GPS). Custom conditions can be defined by the patient 102. The patient 102 also can define one or more profiles 138, each of which can be used to enable one or more of the policies 136. For example, the patient 102 may have one profile for a primary care physician, another profile for a pharmacist, another profile for emergency rooms, and another profile for a specialist (e.g., an oncologist). The patient 102 can enable/disable profiles via the PHR wallet device application 114.

From operation 208, the method 200 proceeds to operation 210. At operation 210, the patient device 112 initiates, via PHR wallet device application 114, a transfer of at least a portion of the PHR 104 from the PHR data store 116 to one or more health care providers 110. In the example shown in FIG. 1, the patient device has initiated transfer of the PHR portion$_1$ 124A to the health care providers 110A and the PHR portion 124B to the health care provider$_2$ 110B. In some embodiments, this transfer is initiated based upon a trigger, such as a time-based trigger or a location-based trigger. Other triggers include an interface between the patient device 112 and a provider device 128, such as via BLUETOOTH, NFC, QR code, or the like.

From operation 210, the method 200 proceeds to operation 212. The method 200 can end at operation 212.

Figure 3:
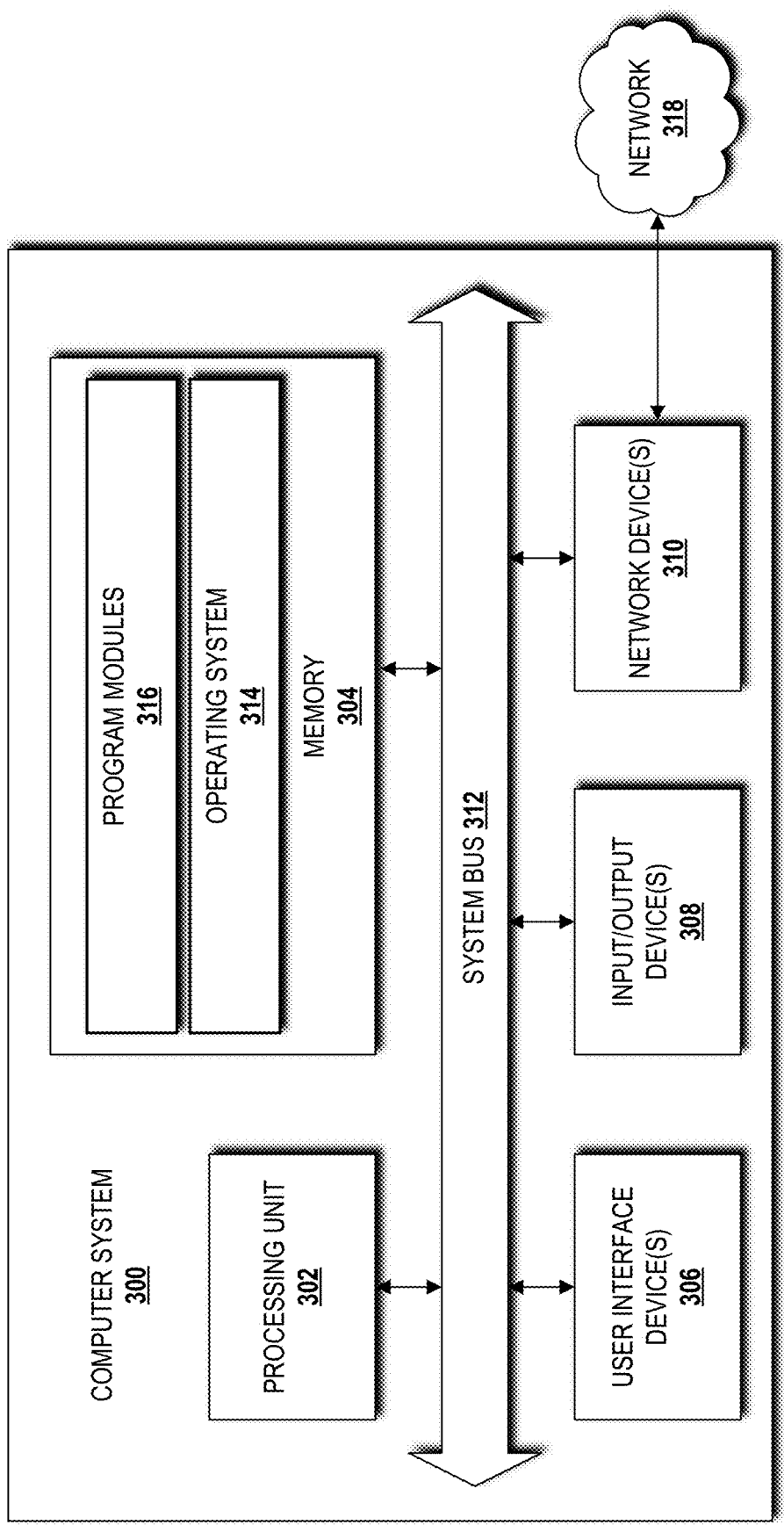
FIG. 3 is a block diagram illustrating an example computer system and components thereof capable of implementing aspects of the embodiments presented herein.

Turning now to FIG. 3 is a block diagram illustrating a computer system 300 configured to provide the functionality in accordance with various embodiments of the concepts and technologies disclosed herein. The systems, devices, and other components disclosed herein, such as the patient device 112, the PHR data store 116, components of the cloud network 118, the provider device(s) 128, or some combination thereof can be implemented, at least in part, using an architecture that is the same as or similar to the architecture of the computer system 300. It should be understood, however, that modification to the architecture may be made to facilitate certain interactions among elements described herein.

The computer system 300 includes a processing unit 302, a memory 304, one or more user interface devices 306, one or more input/output ("I/O") devices 308, and one or more network devices 310, each of which is operatively connected to a system bus 312. The bus 312 enables bi-directional communication between the processing unit 302, the memory 304, the user interface devices 306, the I/O devices 308, and the network devices 310.

The processing unit 302 may be a standard central processor that performs arithmetic and logical operations, a more specific purpose programmable logic controller ("PLC"), a programmable gate array, or other type of processor known to those skilled in the art and suitable for controlling the operation of the server computer. Processing units are generally known, and therefore are not described in further detail herein.

The memory 304 communicates with the processing unit 302 via the system bus 312. In some embodiments, the memory 304 is operatively connected to a memory controller (not shown) that enables communication with the processing unit 302 via the system bus 312. The illustrated memory 304 includes an operating system 314 and one or more program modules 316. The operating system 314 can include, but is not limited to, members of the WINDOWS, WINDOWS CE, and/or WINDOWS MOBILE families of operating systems from MICROSOFT CORPORATION, the LINUX family of operating systems, the SYMBIAN family of operating systems from SYMBIAN LIMITED, the BREW family of operating systems from QUALCOMM CORPORATION, the MAC OS, OS X, and/or iOS families of operating systems from APPLE CORPORATION, the FREEBSD family of operating systems, the SOLARIS family of operating systems from ORACLE CORPORATION, other operating systems, and the like.

The program modules 316 may include various software and/or program modules to perform the various operations described herein. For example, the program modules 316 can include the PHR wallet device application 114, the PHR data store application 122, and the PHR wallet provider application 126 in various embodiments. The program modules 316 and/or other programs can be embodied in computer-readable media containing instructions that, when executed by the processing unit 302, perform various operations such as those described herein. According to embodiments, the program modules 316 may be embodied in hardware, software, firmware, or any combination thereof.

By way of example, and not limitation, computer-readable media may include any available computer storage media or communication media that can be accessed by the computer system 300. Communication media includes computer-readable instructions, data structures, program modules, or other data in a modulated data signal such as a carrier wave or other transport mechanism and includes any delivery media. The term "modulated data signal" means a signal that has one or more of its characteristics changed or set in a manner as to encode information in the signal. By way of example, and not limitation, communication media includes wired media such as a wired network or direct-wired connection, and wireless media such as acoustic, RF, infrared and other wireless media. Combinations of any of the above should also be included within the scope of computer-readable media.

Computer storage media includes volatile and non-volatile, removable and non-removable media implemented in any method or technology for storage of information such as computer-readable instructions, data structures, program modules, or other data. Computer storage media includes, but is not limited to, RAM, ROM, Erasable Programmable ROM ("EPROM"), Electrically Erasable Programmable ROM ("EEPROM"), flash memory or other solid state memory technology, CD-ROM, digital versatile disks ("DVD"), or other optical storage, magnetic cassettes, magnetic tape, magnetic disk storage or other magnetic storage devices, or any other medium which can be used to store the desired information and which can be accessed by the computer system 300. In the claims, the phrase "computer storage medium," "computer-readable storage medium," and variations thereof does not include waves or signals per se and/or communication media, and therefore should be construed as being directed to "non-transitory" media only.

The user interface devices 306 may include one or more devices with which a user accesses the computer system 300. The user interface devices 306 may include, but are not limited to, computers, servers, PDAs, cellular phones, or any suitable computing devices. The I/O devices 308 enable a user to interface with the program modules 316. In one embodiment, the I/O devices 308 are operatively connected to an I/O controller (not shown) that enables communication with the processing unit 302 via the system bus 312. The I/O devices 308 may include one or more input devices, such as, but not limited to, a keyboard, a mouse, or an electronic stylus. Further, the I/O devices 308 may include one or more output devices, such as, but not limited to, a display screen or a printer. In some embodiments, the I/O devices 308 can be used for manual controls for operations to exercise under certain emergency situations.

The network devices 310 enable the computer system 300 to communicate with other networks or remote systems via a network 318, such as communications network 120 and/or the cloud network 118. Examples of the network devices 310 include, but are not limited to, a modem, a radio frequency ("RF") or infrared ("IR") transceiver, a telephonic interface, a bridge, a router, or a network card. The network 318 may be or may include a wireless network such as, but not limited to, a cellular network, a Wireless Local Area Network ("WLAN"), a Wireless Wide Area Network ("WWAN"), a Wireless Personal Area Network ("WPAN") such as provided via BLUETOOTH technology, a Wireless Metropolitan Area Network ("WMAN") such as a WiMAX network or metropolitan cellular network. Alternatively, the network 318 may be or may include a wired network such as, but not limited to, a Wide Area Network ("WAN"), a wired Personal Area Network ("PAN"), or a wired Metropolitan Area Network ("MAN").

Turning now to FIG. 4, an illustrative mobile device 400 and components thereof will be described. In some embodiments, the patient device 112 and/or the provider device(s) 128 described above with reference to FIG. 1 can be configured as and/or can have an architecture similar or identical to the mobile device 400 described herein in FIG. 4. It should be understood, however, that the patient device 112 and/or the provider device(s) 128 may or may not include the functionality described herein with reference to FIG. 4. While connections are not shown between the various components illustrated in FIG. 4, it should be understood that some, none, or all of the components illustrated in FIG. 4 can be configured to interact with one another to carry out various device functions. In some embodiments, the components are arranged so as to communicate via one or more busses (not shown). Thus, it should be understood that FIG. 4 and the following description are intended to provide a general understanding of a suitable environment in which various aspects of embodiments can be implemented, and should not be construed as being limiting in any way.

As illustrated in FIG. 4, the mobile device 400 can include a display 402 for displaying data. According to various embodiments, the display 402 can be configured to display information associated with the PHR wallet device application 114, information associated with the PHR wallet provider application 126, the PHR 104 or a portion thereof including any personal identifying data 106 and/or health data 108, network connection information, various GUI elements, text, images, video, virtual keypads and/or keyboards, messaging data, notification messages, metadata, Internet content, device status, time, date, calendar data, device preferences, map and location data, combinations thereof, and/or the like. The mobile device 400 also can include a processor 404 and a memory or other data storage device ("memory") 406. The processor 404 can be configured to process data and/or can execute computer-executable instructions stored in the memory 406. The computer-executable instructions executed by the processor 404 can include, for example, an operating system 408, one or more applications 410, other computer-executable instructions stored in the memory 406, or the like. In some embodiments, the applications 410 also can include a UI application (not illustrated in FIG. 4).

The UI application can interface with the operating system 408 to facilitate user interaction with functionality and/or data stored at the mobile device 400 and/or stored elsewhere. In some embodiments, the operating system 408 can include a member of the SYMBIAN OS family of operating systems from SYMBIAN LIMITED, a member of the WINDOWS MOBILE OS and/or WINDOWS PHONE OS families of operating systems from MICROSOFT CORPORATION, a member of the PALM WEBOS family of operating systems from HEWLETT PACKARD CORPORATION, a member of the BLACKBERRY OS family of operating systems from RESEARCH IN MOTION LIMITED, a member of the IOS family of operating systems from APPLE INC., a member of the ANDROID OS family of operating systems from GOOGLE INC., and/or other operating systems. These operating systems are merely illustrative of some contemplated operating systems that may be used in accordance with various embodiments of the concepts and technologies described herein and therefore should not be construed as being limiting in any way.

The UI application can be executed by the processor 403 to aid a user in data communications, entering/deleting data, entering and setting user IDs and passwords for device access, configuring settings, manipulating content and/or settings, multimode interaction, interacting with other applications 410, and otherwise facilitating user interaction with the operating system 408, the applications 410, and/or other types or instances of data 412 that can be stored at the mobile device 400.

The applications 410, the data 412, and/or portions thereof can be stored in the memory 406 and/or in a firmware 414, and can be executed by the processor 404. The firmware 414 also can store code for execution during device power up and power down operations. It can be appreciated that the firmware 414 can be stored in a volatile or non-volatile data storage device including, but not limited to, the memory 406 and/or a portion thereof.

The mobile device 400 also can include an input/output ("I/O") interface 416. The I/O interface 416 can be configured to support the input/output of data such as location information, presence status information, user IDs, passwords, and application initiation (start-up) requests. In some embodiments, the I/O interface 416 can include a hardwire connection such as a universal serial bus ("USB") port, a mini-USB port, a micro-USB port, an audio jack, a PS2 port, an IEEE 1394 ("FIREWIRE") port, a serial port, a parallel port, an Ethernet (RJ45) port, an RJ11 port, a proprietary port, combinations thereof, or the like. In some embodiments, the mobile device 400 can be configured to synchronize with another device to transfer content to and/or from the mobile device 400. In some embodiments, the mobile device 400 can be configured to receive updates to one or more of the applications 410 via the I/O interface 416, though this is not necessarily the case. In some embodiments, the I/O interface 416 accepts I/O devices such as keyboards, keypads, mice, interface tethers, printers, plotters, external storage, touch/multi-touch screens, touch pads, trackballs, joysticks, microphones, remote control devices, displays, projectors, medical equipment (e.g., stethoscopes, heart monitors, and other health metric monitors), modems, routers, external power sources, docking stations, combinations thereof, and the like. It should be appreciated that the I/O interface 416 may be used for communications between the mobile device 400 and a network device or local device.

The mobile device 400 also can include a communications component 418. The communications component 418 can be configured to interface with the processor 404 to facilitate wired and/or wireless communications with one or more networks. In some embodiments, the communications component 418 includes a multimode communications subsystem for facilitating communications via the cellular network and one or more other networks.

The communications component 418, in some embodiments, includes one or more transceivers. The one or more transceivers, if included, can be configured to communicate over the same and/or different wireless technology standards with respect to one another. For example, in some embodiments, one or more of the transceivers of the communications component 418 may be configured to communicate using GSM, CDMAONE, CDMA2000, UMTS, LTE, non-3GPP, and various other 2G, 3G, 4G, 5G, 6G, and greater generation technology standards. Moreover, the communications component 418 may facilitate communications over various channel access methods (which may or may not be used by the aforementioned standards) including, but not limited to, TDMA, FDMA, W-CDMA, OFDM, SDMA, and the like.

In addition, the communications component 418 may facilitate data communications using GPRS, EDGE, the HSPA protocol family including HSDPA, EUL or otherwise termed HSUPA, HSPA+, and various other current and future wireless data access standards. In the illustrated embodiment, the communications component 418 can include a first transceiver ("TxRx") 420A that can operate in a first communications mode (e.g., GSM). The communications component 418 also can include an Nth transceiver ("TxRx") 420N that can operate in a second communications mode relative to the first transceiver 420A (e.g., UMTS). While two transceivers 420A-420N (hereinafter collectively and/or generically referred to as "transceivers 420") are shown in FIG. 4, it should be appreciated that less than two, two, and/or more than two transceivers 420 can be included in the communications component 418.

The communications component 418 also can include an alternative transceiver ("Alt TxRx") 422 for supporting other types and/or standards of communications. According to various contemplated embodiments, the alternative transceiver 422 can communicate using various communications technologies such as, for example, WI-FI, WIMAX, BLUETOOTH, infrared, infrared data association ("IRDA"), near field communications ("NFC"), other RF technologies, combinations thereof, and the like. In some embodiments, the communications component 418 also can facilitate reception from terrestrial radio networks, digital satellite radio networks, internet-based radio service networks, combinations thereof, and the like. The communications component 418 can process data from a network such as the Internet, an intranet, a broadband network, a WI-FI hotspot, an Internet service provider ("ISP"), a digital subscriber line ("DSL") provider, a broadband provider, combinations thereof, or the like.

The mobile device 400 also can include one or more sensors 423. The sensors 423 can include temperature sensors, light sensors, air quality sensors, movement sensors, accelerometers, magnetometers, gyroscopes, infrared sensors, orientation sensors, noise sensors, microphones proximity sensors, combinations thereof, and/or the like. Additionally, audio capabilities for the mobile device 400 may be provided by an audio I/O component 426. The audio I/O component 426 of the mobile device 400 can include one or more speakers for the output of audio signals, one or more microphones for the collection and/or input of audio signals, and/or other audio input and/or output devices.

The illustrated mobile device 400 also can include a subscriber identity module ("SIM") system 428. The SIM system 428 can include a universal SIM ("USIM"), a universal integrated circuit card ("UICC") and/or other identity devices. The SIM system 428 can include and/or can be connected to or inserted into an interface such as a slot interface 430. In some embodiments, the slot interface 430 can be configured to accept insertion of other identity cards or modules for accessing various types of networks. Additionally, or alternatively, the slot interface 430 can be configured to accept multiple subscriber identity cards.

Because other devices and/or modules for identifying users and/or the mobile device 400 are contemplated, it should be understood that these embodiments are illustrative, and should not be construed as being limiting in any way.

The mobile device 400 also can include an image capture and processing system 432 ("image system"). The image system 432 can be configured to capture or otherwise obtain photos, videos, and/or other visual information. As such, the image system 432 can include cameras, lenses, charge-coupled devices ("CCDs"), combinations thereof, or the like. The mobile device 400 may also include a video system 434. The video system 434 can be configured to capture, process, record, modify, and/or store video content. Photos and videos obtained using the image system 432 and the video system 434, respectively, may be added as message content to an MMS message, email message, and sent to another device. The video and/or photo content also can be shared with other devices via various types of data transfers via wired and/or wireless communication devices as described herein.

The mobile device 400 also can include one or more location components 436. The location components 436 can be configured to send and/or receive signals to determine a geographic location of the mobile device 400. According to various embodiments, the location components 436 can send and/or receive signals from global positioning system ("GPS") devices, assisted-GPS ("A-GPS") devices, WI-FI/WIMAX and/or cellular network triangulation data, combinations thereof, and the like. The location component 436 also can be configured to communicate with the communications component 418 to retrieve triangulation data for determining a location of the mobile device 400. In some embodiments, the location component 436 can interface with cellular network nodes, telephone lines, satellites, location transmitters and/or beacons, wireless network transmitters and receivers, combinations thereof, and the like. In some embodiments, the location component 436 can include and/or can communicate with one or more of the sensors 424 such as a compass, an accelerometer, and/or a gyroscope to determine the orientation of the mobile device 400. Using the location component 436, the mobile device 400 can generate and/or receive data to identify its geographic location, or to transmit data used by other devices to determine the location of the mobile device 400. The location component 436 may include multiple components for determining the location and/or orientation of the mobile device 400.

The illustrated mobile device 400 also can include a power source 438. The power source 438 can include one or more batteries, power supplies, power cells, and/or other power subsystems including alternating current ("AC") and/or direct current ("DC") power devices. The power source 438 also can interface with an external power system or charging equipment via a power I/O component 430. Because the mobile device 400 can include additional and/or alternative components, the above embodiment should be understood as being illustrative of one possible operating environment for various embodiments of the concepts and technologies described herein. The described embodiment of the mobile device 400 is illustrative, and should not be construed as being limiting in any way.

As used herein, communication media includes computer-executable instructions, data structures, program modules, or other data in a modulated data signal such as a carrier wave or other transport mechanism and includes any delivery media. The term "modulated data signal" means a signal that has one or more of its characteristics changed or set in a manner as to encode information in the signal. By way of example, and not limitation, communication media includes wired media such as a wired network or direct-wired connection, and wireless media such as acoustic, RF, infrared, and other wireless media. Combinations of any of the above should also be included within the scope of computer-readable media.

By way of example, and not limitation, computer storage media may include volatile and non-volatile, removable and non-removable media implemented in any method or technology for storage of information such as computer-executable instructions, data structures, program modules, or other data. For example, computer media includes, but is not limited to, RAM, ROM, EPROM, EEPROM, flash memory or other solid state memory technology, CD-ROM, digital versatile disks ("DVD"), HD-DVD, BLU-RAY, or other optical storage, magnetic cassettes, magnetic tape, magnetic disk storage or other magnetic storage devices, or any other medium which can be used to store the desired information and which can be accessed by the mobile device 400 or other devices or computers described herein, such as the computer system 300 described above with reference to FIG. 3. In the claims, the phrase "computer storage medium," "computer-readable storage medium," and variations thereof does not include waves or signals per se and/or communication media, and therefore should be construed as being directed to "non-transitory" media only.

Encoding the software modules presented herein also may transform the physical structure of the computer-readable media presented herein. The specific transformation of physical structure may depend on various factors, in different implementations of this description. Examples of such factors may include, but are not limited to, the technology used to implement the computer-readable media, whether the computer-readable media is characterized as primary or secondary storage, and the like. For example, if the computer-readable media is implemented as semiconductor-based memory, the software disclosed herein may be encoded on the computer-readable media by transforming the physical state of the semiconductor memory. For example, the software may transform the state of transistors, capacitors, or other discrete circuit elements constituting the semiconductor memory. The software also may transform the physical state of such components in order to store data thereupon.

As another example, the computer-readable media disclosed herein may be implemented using magnetic or optical technology. In such implementations, the software presented herein may transform the physical state of magnetic or optical media, when the software is encoded therein. These transformations may include altering the magnetic characteristics of particular locations within given magnetic media. These transformations also may include altering the physical features or characteristics of particular locations within given optical media, to change the optical characteristics of those locations. Other transformations of physical media are possible without departing from the scope and spirit of the present description, with the foregoing examples provided only to facilitate this discussion.

In light of the above, it should be appreciated that many types of physical transformations may take place in the mobile device 400 in order to store and execute the software components presented herein. It is also contemplated that the mobile device 400 may not include all of the components shown in FIG. 4, may include other components that are not explicitly shown in FIG. 4, or may utilize an architecture completely different than that shown in FIG. 4.

Figure 5:
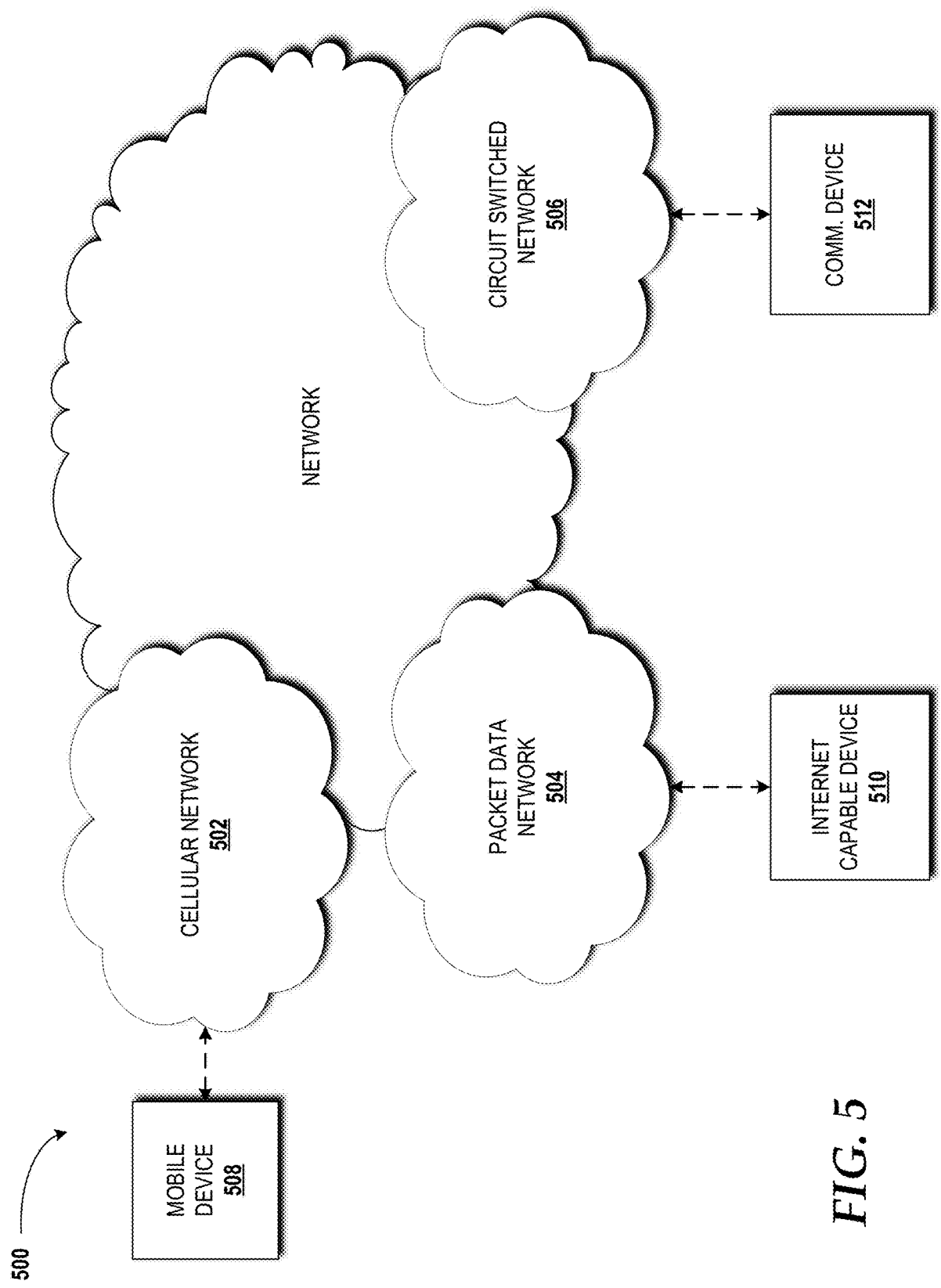
FIG. 5 is a block diagram illustrating an example network capable of implementing aspects of the embodiments presented herein.

Turning now to FIG. 5, details of a network 500 are illustrated, according to an illustrative embodiment. In some embodiments, the network 500 can include the communications network 120 and/or the cloud network 118. The network 500 includes a cellular network 502, a packet data network 504, for example, the Internet, and a circuit switched network 506, for example, a public switched telephone network ("PSTN"). The cellular network 502 includes various components such as, but not limited to, base transceiver stations ("BTSs"), NBs or eNBs, combination eNB/gNB, base station controllers ("BSCs"), radio network controllers ("RNCs"), mobile switching centers ("MSCs"), MMEs, short message service centers ("SMSCs"), multimedia messaging service centers ("MMSCs"), home location registers ("HLRs"), HSSs, VLRs"), charging platforms, billing platforms, voicemail platforms, GPRS core network components, location service nodes, control plane functions such as access and mobility management function ("AMF"), user plane functions such as ("UPF"), an IP Multimedia Subsystem ("IMS"), and the like. The cellular network 502 also includes radios and nodes for receiving and transmitting voice, data, and combinations thereof to and from radio transceivers, networks, the packet data network 503, and the circuit switched network 506.

A mobile communications device 508, such as, for example, the patient device 112, the provider device(s) 128, a cellular telephone, a user equipment, a mobile terminal, a PDA, a laptop computer, a handheld computer, and combinations thereof, can be operatively connected to the cellular network 502. The cellular network 502 can be configured as a 2G GSM network and can provide data communications via GPRS and/or EDGE. Additionally, or alternatively, the cellular network 502 can be configured as a 3G UMTS network and can provide data communications via the HSPA protocol family, for example, HSDPA, EUL (also referred to as HSUPA), and HSPA+. The cellular network 502 also is compatible with 3G mobile communications standards such as LTE, or the like, as well as evolved and future mobile standards.

The packet data network 504 includes various devices, for example, servers, computers, databases, and other devices in communication with one another, as is generally known. The packet data network 504 devices are accessible via one or more network links. The servers often store various files that are provided to a requesting device such as, for example, a computer, a terminal, a smartphone, or the like. Typically, the requesting device includes software (a "browser") for executing a web page in a format readable by the browser or other software. Other files and/or data may be accessible via "links" in the retrieved files, as is generally known. In some embodiments, the packet data network 504 includes or is in communication with the Internet. The circuit switched network 506 includes various hardware and software for providing circuit switched communications. The circuit switched network 506 may include, or may be, what is often referred to as a plain old telephone system ("POTS"). The functionality of a circuit switched network 506 or other circuit-switched network are generally known and will not be described herein in detail.

The illustrated cellular network 502 is shown in communication with the packet data network 504 and a circuit switched network 506, though it should be appreciated that this is not necessarily the case. One or more Internet-capable devices 510, for example, the patient device 112, the provider device(s) 128, a PC, a laptop, a portable device$_n$, or another suitable device$_n$ can communicate with one or more cellular networks 502, and devices connected thereto, through the packet data network 504. It also should be appreciated that the Internet-capable device 510 can communicate with the packet data network 504 through the circuit switched network 506, the cellular network 502, and/or via other networks (not illustrated).

As illustrated, a communications device 512, for example, a telephone, facsimile machine, modem, computer, or the like, can be in communication with the circuit switched network 506, and therethrough to the packet data network 504 and/or the cellular network 502. It should be appreciated that the communications device 512 can be an Internet-capable device$_n$ and can be substantially similar to the Internet-capable device 510. In the specification, the network is used to refer broadly to any combination of the networks 502, 504, 506 shown in FIG. 5. It should be appreciated that substantially all of the functionality described with reference to the communications network 120 and the cloud network 118 can be performed by the cellular network 502, the packet data network 503, and/or the circuit switched network 506, alone or in combination with other networks, network elements, and the like.

Figure 6:
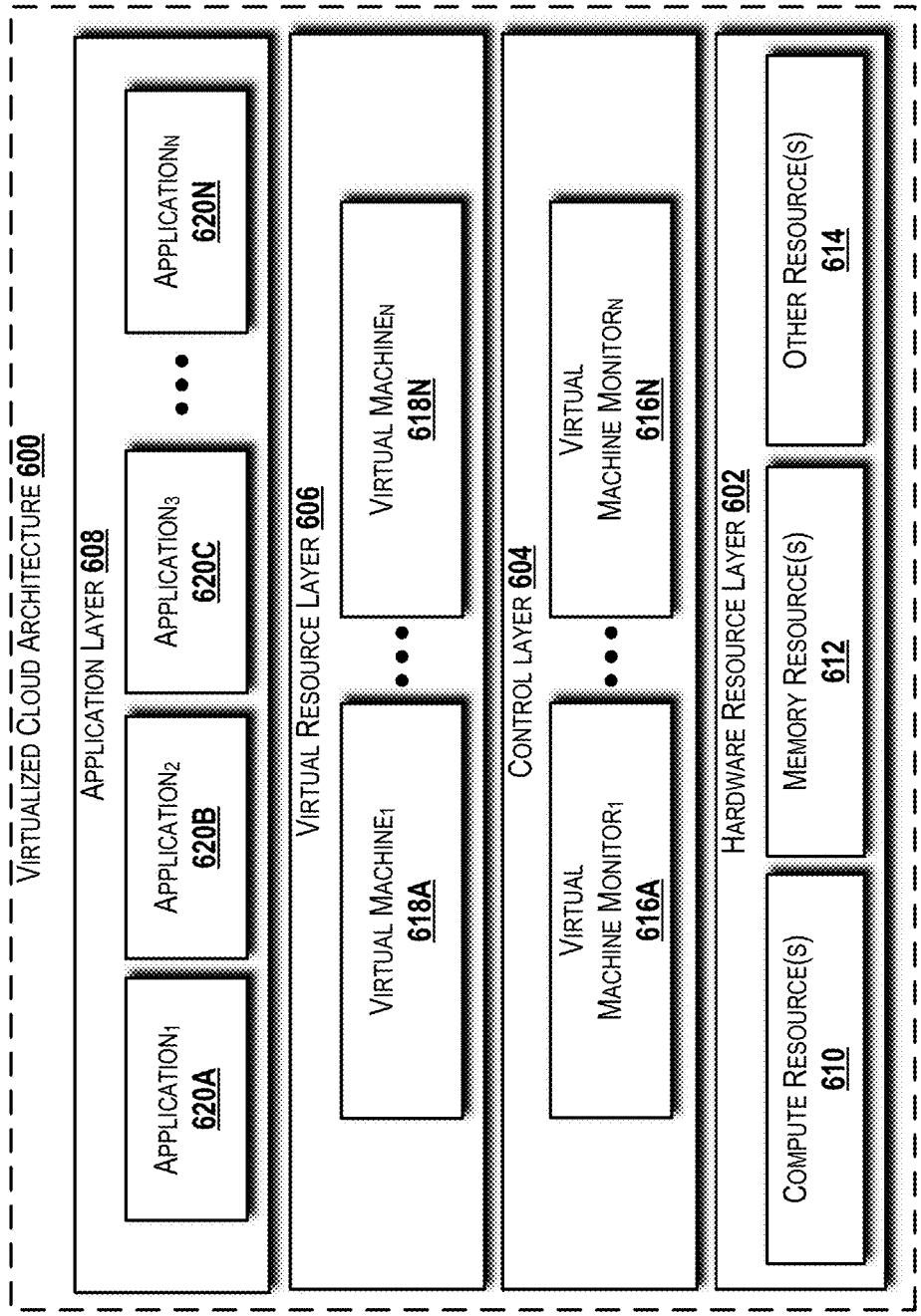
FIG. 6 is a block diagram illustrating an example virtualized cloud architecture capable of implementing aspects of the embodiments presented herein.

Turning now to FIG. 6, a block diagram illustrating an example virtualized cloud architecture 600 and components thereof will be described, according to an exemplary embodiment. In some embodiments, the virtualized cloud architecture 600 can be utilized to implement, at least in part, the cloud network 118, including the PHR data store 116. The virtualized cloud architecture 600 is a shared infrastructure that can support multiple services and network applications. The illustrated virtualized cloud architecture 600 includes a hardware resource layer 602, a control layer 604, a virtual resource layer 606, and an application layer 608 that work together to perform operations as will be described in detail herein.

The hardware resource layer 602 provides hardware resources, which, in the illustrated embodiment, include one or more compute resources 610, one or more memory resources 612, and one or more other resources 614. The compute resource(s) 610 can include one or more hardware components that perform computations to process data, and/or to execute computer-executable instructions of one or more application programs, operating systems, and/or other software. The compute resources 610 can include one or more central processing units ("CPUs") configured with one or more processing cores. The compute resources 610 can include one or more graphics processing unit ("GPU") configured to accelerate operations performed by one or more CPUs, and/or to perform computations to process data, and/or to execute computer-executable instructions of one or more application programs, operating systems, and/or other software that may or may not include instructions particular to graphics computations. In some embodiments, the compute resources 610 can include one or more discrete GPUs. In some other embodiments, the compute resources 610 can include CPU and GPU components that are configured in accordance with a co-processing CPU/GPU computing model, wherein the sequential part of an application executes on the CPU and the computationally-intensive part is accelerated by the GPU. The compute resources 610 can include one or more system-on-chip ("SoC") components along with one or more other components, including, for example, one or more of the memory resources 612, and/or one or more of the other resources 614. In some embodiments, the compute resources 610 can be or can include one or more SNAPDRAGON SoCs, available from QUAL-COMM; one or more TEGRA SoCs, available from NVIDIA; one or more HUMMINGBIRD SoCs, available from SAMSUNG; one or more Open Multimedia Application Platform ("OMAP") SoCs, available from TEXAS INSTRUMENTS; one or more customized versions of any of the above SoCs; and/or one or more proprietary SoCs. The compute resources 610 can be or can include one or more hardware components architected in accordance with an advanced reduced instruction set computing ("RISC") machine ("ARM") architecture, available for license from ARM HOLDINGS. Alternatively, the compute resources 610 can be or can include one or more hardware components architected in accordance with an x86 architecture, such an architecture available from INTEL CORPORATION of Mountain View, California, and others. Those skilled in the art will appreciate the implementation of the compute resources 610 can utilize various computation architectures, and as such, the compute resources 610 should not be construed as being limited to any particular computation architecture or combination of computation architectures, including those explicitly disclosed herein.

The memory resource(s) 612 can include one or more hardware components that perform storage operations, including temporary or permanent storage operations. In some embodiments, the memory resource(s) 612 include volatile and/or non-volatile memory implemented in any method or technology for storage of information such as computer-readable instructions, data structures, program modules, or other data disclosed herein.

Computer storage media includes, but is not limited to, random access memory ("RAM"), read-only memory ("ROM"), Erasable Programmable ROM ("EPROM"), Electrically Erasable Programmable ROM ("EEPROM"), flash memory or other solid state memory technology, CD-ROM, digital versatile disks ("DVD"), or other optical storage, magnetic cassettes, magnetic tape, magnetic disk storage or other magnetic storage devices, or any other medium which can be used to store data and which can be accessed by the compute resources 610.

The other resource(s) 614 can include any other hardware resources that can be utilized by the compute resources(s) 610 and/or the memory resource(s) 612 to perform operations described herein. The other resource(s) 614 can include one or more input and/or output processors (e.g., network interface controller or wireless radio), one or more modems, one or more codec chipset, one or more pipeline processors, one or more fast Fourier transform ("FFT") processors, one or more digital signal processors ("DSPs"), one or more speech synthesizers, and/or the like.

The hardware resources operating within the hardware resource layer 602 can be virtualized by one or more virtual machine monitors ("VMMs") 616A-616N (also known as "hypervisors;" hereinafter "VMMs 616") operating within the control layer 604 to manage one or more virtual resources that reside in the virtual resource layer 606. The VMMs 616 can be or can include software, firmware, and/or hardware that alone or in combination with other software, firmware, and/or hardware, manages one or more virtual resources operating within the virtual resource layer 606.

The virtual resources operating within the virtual resource layer 606 can include abstractions of at least a portion of the compute resources 610, the memory resources 612, the other resources 614, or any combination thereof. These abstractions are referred to herein as virtual machines ("VMs"). In the illustrated embodiment, the virtual resource layer 606 includes VMs 618A-618N (hereinafter "VMs 618"). Each of the VMs 618 can execute one or more applications 620A-620N in the application layer 608.

Based on the foregoing, it should be appreciated that concepts and technologies directed to secure user-controlled personal health records have been disclosed herein. Although the subject matter presented herein has been described in language specific to computer structural features, methodological and transformative acts, specific computing machinery, and computer-readable media, it is to be understood that the concepts and technologies disclosed herein are not necessarily limited to the specific features, acts, or media described herein. Rather, the specific features, acts and mediums are disclosed as example forms of implementing the concepts and technologies disclosed herein.

The subject matter described above is provided by way of illustration only and should not be construed as limiting. Various modifications and changes may be made to the subject matter described herein without following the example embodiments and applications illustrated and described, and without departing from the true spirit and scope of the embodiments of the concepts and technologies disclosed herein.

The invention claimed is:

1. A method comprising:
   receiving, by a patient device comprising a processor, a calendar entry associated with an event to be added to a calendar application executed by the patient device, wherein the calendar entry specifies that a personal health record wallet device application stored on the patient device be launched based on a time associated with the event of the calendar entry;
   obtaining, by the patient device, the time associated with the event from the calendar application executed by the patient device, wherein the event is associated with a health care provider;
   when a current time matches the time associated with the event obtained from the calendar application, launching, by the patient device, the personal health record wallet device application stored on the patient device, wherein the personal health record wallet device application provides an interface through which a user of the patient device can control access to a personal health record associated with the user;
   connecting, by the patient device, via the personal health record wallet device application, to a personal health record server that stores the personal health record associated with the user;
   defining, by the patient device, via the personal health record wallet device application, an access level to be applied to the personal health record; and
   initiating, by the patient device, via the personal health record wallet device application, a transfer of the personal health record from the personal health record server to the health care provider, wherein the health care provider is permitted to access a portion of the personal health record in accordance with the access level.

2. The method of claim 1, wherein the personal health record comprises personal identifying information and health data.

3. The method of claim 2, wherein the access level permits access to at least one of at least a portion of the health data or at least a portion of the personal identifying information.

4. The method of claim 1, wherein initiating a transfer of the personal health record from the personal health record server to a health care provider comprises presenting, on a display of the patient device, a code that can be scanned by a provider device associated with the health care provider to grant permission for the personal health record to be transferred to the health care provider.

5. The method of claim 1, wherein defining, by the patient device, via the personal health record wallet device application, the access level to be applied to the personal health record comprises defining, by the patient device, via the personal health record wallet device application, a policy that specifies a plurality of access levels and a condition under which each access level of the plurality of access levels is to be applied, wherein the plurality of access levels comprises the access level.

6. The method of claim 5, wherein the condition defines a type of health care provider, a time period, or a trigger event.

7. The method of claim 5, further comprising assigning the policy to a profile.

8. The method of claim 1, further comprising receiving, by the patient device, a notification identifying new health data to be added to the personal health record, wherein the new health data is provided, at least in part, by the health care provider.

9. The method of claim 1, further comprising disabling, by the patient device, via the personal health record wallet device application, access to the personal health record by the health care provider.

10. A computer-readable storage medium comprising computer-executable instructions that, when executed by a processor of a patient device, cause the processor to perform operations comprising:
    receiving a calendar entry associated with an event to be added to a calendar application executed by the patient device, wherein the calendar entry specifies that a personal health record wallet device application stored on the patient device be launched based on a time associated with the event of the calendar entry;
    obtaining the time associated with the event from the calendar application executed by the patient device, wherein the event is associated with a health care provider;
    when a current time matches the time associated with the event obtained from the calendar application, launching the personal health record wallet device application stored on the patient device, wherein the personal health record wallet device application provides an interface through which a user of the patient device can control access to a personal health record associated with the user;
    connecting, via the personal health record wallet device application, to a personal health record server that stores the personal health record associated with the user;
    defining, via the personal health record wallet device application, an access level to be applied to the personal health record; and
    initiating, via the personal health record wallet device application, a transfer of the personal health record from the personal health record server to the health care provider, wherein the health care provider is permitted to access a portion of the personal health record in accordance with the access level.

11. The computer-readable storage medium of claim 10, wherein the personal health record comprises personal identifying information and health data.

12. The computer-readable storage medium of claim 11, wherein the access level permits access to at least one of at least a portion of the health data or at least a portion of the personal identifying information.

13. The computer-readable storage medium of claim 10, wherein initiating a transfer of the personal health record from the personal health record server to a health care provider comprises presenting, on a display of the patient device, a code that can be scanned by a provider device associated with the health care provider to grant permission for the personal health record to be transferred to the health care provider.

14. The computer-readable storage medium of claim 13, wherein defining, via the personal health record wallet device application, the access level to be applied to the personal health record comprises defining, via the personal health record wallet device application, a policy that specifies a plurality of access levels and a condition under which each access level of the plurality of access levels is to be applied, wherein the plurality of access levels comprises the access level.

15. The computer-readable storage medium of claim 14, wherein the condition defines a type of health care provider, a time period, or a trigger event.

16. The computer-readable storage medium of claim 14, wherein the operations further comprise assigning the policy to a profile.

17. The computer-readable storage medium of claim 10, wherein the operations further comprise receiving a notification identifying new health data to be added to the personal health record, wherein the new health data is provided, at least in part, by the health care provider.

18. The computer-readable storage medium of claim 10, wherein the operations further comprise disabling, via the personal health record wallet device application, access to the personal health record by the health care provider.

19. A patient device comprising:
a processor; and
a memory having instructions of a personal health record wallet device application stored thereon, wherein the instructions, when executed by the processor, cause the processor to perform operations comprising receiving a calendar entry associated with an event to be added to a calendar application executed by the patient device, wherein the calendar entry specifies that the personal health record wallet device application stored on the patient device be launched based on a time associated with the event of the calendar entry, obtaining the time associated with the event from the calendar application executed by the patient device, wherein the event is associated with a health care provider, when a current time matching the time associated with the event obtained from the calendar application, launching the personal health record wallet device application stored on the patient device, wherein the personal health record wallet device application provides an interface through which a user of the patient device can control access to a personal health record associated with the user, connecting to a personal health record server that stores the personal health record associated with the user, defining an access level to be applied to the personal health record, and initiating a transfer of the personal health record from the personal health record server to the health care provider, wherein the health care provider is permitted to access a portion of the personal health record in accordance with the access level.

20. The patient device of claim 19, wherein initiating a transfer of the personal health record from the personal health record server to a health care provider comprises presenting, on a display of the patient device, a code that can be scanned by a provider device associated with the health care provider to grant permission for the personal health record to be transferred to the health care provider.

\* \* \* \* \*